United States Patent
Grootaert et al.

(10) Patent No.: US 9,273,164 B2
(45) Date of Patent: Mar. 1, 2016

(54) CURING COMPOSITIONS FOR FLUOROPOLYMERS

(71) Applicant: 3M INNOVATIVE PROPERTIES COMPANY, St. Paul, MN (US)

(72) Inventors: Werner M. A. Grootaert, Oakdale, MN (US); Michael S. Wendland, North Saint Paul, MN (US); George W. Griesgraber, Eagan, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 14/355,901

(22) PCT Filed: Nov. 7, 2012

(86) PCT No.: PCT/US2012/063896
§ 371 (c)(1),
(2) Date: May 2, 2014

(87) PCT Pub. No.: WO2013/070723
PCT Pub. Date: May 16, 2013

(65) Prior Publication Data
US 2014/0288232 A1    Sep. 25, 2014

Related U.S. Application Data

(60) Provisional application No. 61/557,707, filed on Nov. 9, 2011.

(51) Int. Cl.
| | | |
|---|---|---|
| *C08F 14/26* | (2006.01) | |
| *C08L 27/12* | (2006.01) | |
| *C07C 215/88* | (2006.01) | |
| *C08K 5/18* | (2006.01) | |
| *C08K 3/04* | (2006.01) | |

(52) U.S. Cl.
CPC ............... *C08F 14/26* (2013.01); *C07C 215/88* (2013.01); *C08K 3/04* (2013.01); *C08K 5/18* (2013.01); *C07C 2103/94* (2013.01)

(58) Field of Classification Search
USPC ................. 525/526.3, 380; 524/544
See application file for complete search history.

(56) References Cited

U.S. PATENT DOCUMENTS

| | | | |
|---|---|---|---|
| 4,281,092 A | 7/1981 | Breazeale | |
| 5,554,680 A | 9/1996 | Ojakaar | |
| 5,565,512 A | 10/1996 | Saito et al. | |
| 5,621,145 A | 4/1997 | Saito et al. | |
| 5,700,879 A | 12/1997 | Yamamoto et al. | |
| 5,767,204 A | 6/1998 | Iwa et al. | |
| 5,891,965 A | 4/1999 | Worm et al. | |
| 6,255,535 B1 | 7/2001 | Schulz et al. | |
| 6,255,536 B1 | 7/2001 | Worm et al. | |
| 6,294,627 B1 | 9/2001 | Worm et al. | |
| 6,602,961 B1 | 8/2003 | Saito et al. | |
| 6,890,995 B2 | 5/2005 | Kolb et al. | |
| 7,294,677 B2 | 11/2007 | Grootaert et al. | |
| 7,402,630 B2 | 7/2008 | Grootaert et al. | |
| 2005/0124721 A1* | 6/2005 | Arthur et al. | 523/115 |
| 2005/0124762 A1* | 6/2005 | Cohen et al. | 525/191 |

FOREIGN PATENT DOCUMENTS

| | | | |
|---|---|---|---|
| EP | 0 708 139 A1 | 4/1996 | |
| WO | WO 2006/068685 A1 | 6/2006 | |
| WO | WO-2006/068685 A1 * | 6/2006 | |
| WO | WO 2007/075273 A1 | 7/2007 | |

OTHER PUBLICATIONS

Molteni, Valentina, et al. "A New class of HIV-1 Integrase Inhibitors: The 3,3,3,3- Tetramethy1-1,1-spirobi(indan__-5,5,6,6-tetrol Family", Journal Medical Chemical, vol. 43, No. 10, pp. 2031-2039, May 1, 2000.*

Ma, Xiaohua et al. "Synthesis and Gas Transport Properties of Hydroxyl-Functionalized Polyimides with Intrinsic Microporosity", Macromolecules, vol. 45, No. 9, May 8, 2012, pp. 3841-3849.*

Ma,Xiaohua et al. "Synthesis and Gas Transport Properties of Hydroxyl-Functionalized Polyimides with Intrinsic Microporosity", Macromolecules, vol. 45, No. 9, May 8, 2012, pp. 3841-3849.

International Search Report for International Application No. PCT/US2012/063896, Mailed Nov. 7, 2012, 4 pgs.

* cited by examiner

*Primary Examiner* — Peter D Mulcahy
*Assistant Examiner* — Henry Hu
(74) *Attorney, Agent, or Firm* — C. Michael Geise

(57) ABSTRACT

Diaminospirobisindane diols, curable compositions, curative compositions, cured articles, and methods of curing are described.

14 Claims, No Drawings

CURING COMPOSITIONS FOR FLUOROPOLYMERS

TECHNICAL FIELD

This description relates to a curative composition as well as curable and cured compositions, methods of making cured and curable compositions, articles, and methods of making curatives.

BACKGROUND

Fluoroelastomers are cured or crosslinked and generally are tolerant to high temperatures and harsh chemical environments. They are particularly useful as seals, gaskets, and molded parts in systems that are exposed to elevated temperatures and/or corrosive materials. For sealing applications that require resistance to the most extreme conditions, perfluorinated elastomers are used. Such parts are used in applications such as automotive, chemical processing, semiconductor, aerospace, and petroleum industries, among others.

Fluoroelastomers often include a cure-site component to facilitate cure in the presence of a curative or catalyst. One class of useful cure-site components used in perfluoroelastomers includes nitrile group-containing monomers, for which organotin catalysts have been used as curing components. Such catalysts, however, can leave undesirable extractable metal residues in the cured product and are undesirable for environmental reasons.

Ammonia-generating compounds have also been used as a cure system component in fluoroelastomers. These cure systems, however, lack the desired level of rheology control during processing.

Fluoroalkoxy onium-containing catalysts were developed to address improved compression set performance. These catalysts, however, still lack the desired level of rheology control (i.e. premature curing during processing, often referred to as "scorch") during processing unless additional steps are taken to react these catalysts with additional materials.

SUMMARY

In one aspect, the present description provides curable compositions comprising a fluoroelastomer comprising a nitrogen-containing cure site monomer and a curative selected from the group consisting of curatives of Formula I and II, where Formula I is:

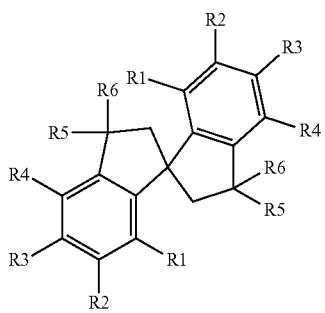

wherein each R1 is independently selected from H, Cl, Br, I, a C1 to C20 linear, cyclic, or branched alkyl group, a C5 to C20 aryl group, a C5 to C20 alkaryl group, a C5 to C20 aralkyl group, and $NH_2$;

each R2 is —OH;

each R3 is independently selected from H, Cl, Br, I, a C1 to C20 linear, cyclic, or branched alkyl group, a C5 to C20 aryl group, a C5 to C20 alkaryl group, a C5 to C20 aralkyl group, and $NH_2$;

each R4 is independently selected from H, Cl, Br, I, a C1 to C20 linear, cyclic, or branched alkyl group, and a C5 to C20 aryl group, a C5 to C20 alkaryl group, a C5 to C20 aralkyl group;

each R5 and R6 is independently selected from an —H, a C1 to C20 linear or branched alkyl group, a C3 to C40 alkyl group that forms a spiro group when both R5 and R6 are part of the same cyclic structure, a C5 to C40 aryl group, a C5 to C40 alkaryl group, a C5 to C40 aralkyl group that optionally forms a spiro group when both R5 and R6 are part of the same cyclic structure, an —OH, and together with one another a C=O;

provided that at least one of R1 and R3 on each ring is an —$NH_2$; and

Formula II is:

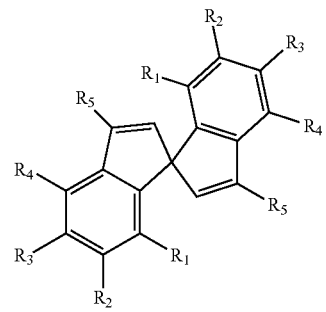

wherein each R1 is independently selected from H, Cl, Br, I, a C1 to C20 linear, cyclic, or branched alkyl group, a C5 to C20 aryl group, a C5 to C20 alkaryl group, a C5 to C20 aralkyl group, and $NH_2$;

each R2 is —OH;

each R3 is independently selected from H, Cl, Br, I, a C1 to C20 linear, cyclic or branched alkyl group, a C5 to C20 aryl group, a C5 to C20 alkaryl group, a C5 to C20 aralkyl group, and $NH_2$;

each R4 is independently selected from H, Cl, Br, I, a C1 to C20 linear, cyclic or branched alkyl group, a C5 to C20 aryl group, a C5 to C20 alkaryl group, and a C5 to C20 aralkyl group;

each R5 is independently selected from an —H, a C1 to C20 linear, cyclic, or branched alkyl group, a C5 to C40 aryl group, a C5 to C40 alkaryl group, and a C5 to C40 aralkyl group;

provided that at least one of R1 and R3 on each ring is an —$NH_2$.

In another aspect, the present description provides methods comprising curing a curable compositions that comprise a fluoroelastomer comprising a nitrogen-containing cure site monomer and a curative selected from the group consisting of curatives of Formula I and II, where Formula I is:

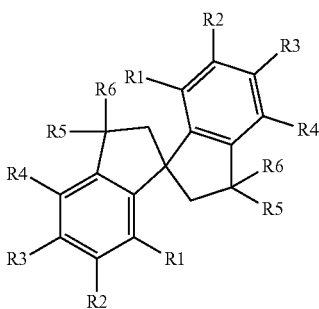

wherein each R1 is independently selected from H, Cl, Br, I, a C1 to C20 linear, cyclic, or branched alkyl group, a C5 to C20 aryl group, a C5 to C20 alkaryl group, a C5 to C20 aralkyl group, and NH$_2$;

each R2 is —OH;

each R3 is independently selected from H, Cl, Br, I, a C1 to C20 linear, cyclic, or branched alkyl group, a C5 to C20 aryl group, a C5 to C20 alkaryl group, a C5 to C20 aralkyl group, and NH$_2$;

each R4 is independently selected from H, Cl, Br, I, a C1 to C20 linear, cyclic, or branched alkyl group, a C5 to C20 aryl group, a C5 to C20 alkaryl group, and a C5 to C20 aralkyl group;

each R5 and R6 is independently selected from an —H, a C1 to C20 linear or branched alkyl group, a C3 to C40 alkyl group that forms a spiro group when both R5 and R6 are part of the same cyclic structure, a C5 to C40 aryl group, a C5 to C40 alkaryl group, a C5 to C40 aralkyl group that optionally forms a spiro group when both R5 and R6 are part of the same cyclic structure, an —OH, and together with one another a C=O;

provided that at least one of R1 and R3 on each ring is an —NH$_2$; and

Formula II is:

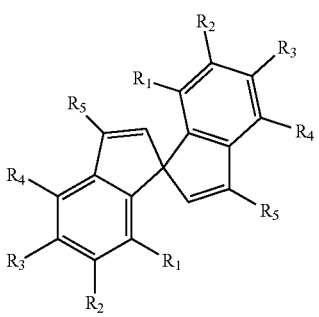

wherein each R1 is independently selected from H, Cl, Br, I, a C1 to C20 linear, cyclic, or branched alkyl group, a C5 to C20 aryl group, a C5 to C20 alkaryl group, a C5 to C20 aralkyl group, and NH$_2$;

each R2 is —OH;

each R3 is independently selected from H, Cl, Br, I, a C1 to C20 linear, cyclic or branched alkyl group, a C5 to C20 aryl group, a C5 to C20 alkaryl group, a C5 to C20 aralkyl group, and NH$_2$;

each R4 is independently selected from H, Cl, Br, I, a C1 to C20 linear, cyclic or branched alkyl group, a C5 to C20 aryl group, a C5 to C20 alkaryl group, and a C5 to C20 aralkyl group;

each R5 is independently selected from an —H, a C1 to C20 linear, cyclic, or branched alkyl group, a C5 to C40 aryl group, a C5 to C40 alkaryl group, and a C5 to C40 aralkyl group;

provided that at least one of R1 and R3 on each ring is an —NH$_2$.

In yet another aspect, the present description provides cured articles prepared by methods comprising curing a curable compositions that comprise a fluoroelastomer comprising a nitrogen-containing cure site monomer and a curative selected from the group consisting of curatives of Formula I and II, where Formula I is:

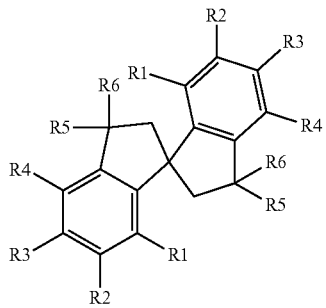

wherein each R1 is independently selected from H, Cl, Br, I, a C1 to C20 linear, cyclic, or branched alkyl group, a C5 to C20 aryl group, a C5 to C20 alkaryl group, a C5 to C20 aralkyl group, and NH$_2$;

each R2 is —OH;

each R3 is independently selected from H, Cl, Br, I, a C1 to C20 linear, cyclic, or branched alkyl group, a C5 to C20 aryl group, a C5 to C20 alkaryl group, a C5 to C20 aralkyl group, and NH$_2$;

each R4 is independently selected from H, Cl, Br, I, a C1 to C20 linear, cyclic, or branched alkyl group, and a C5 to C20 aryl group, a C5 to C20 alkaryl group, and a C5 to C20 aralkyl group;

each R5 and R6 is independently selected from an —H, a C1 to C20 linear or branched alkyl group, a C3 to C40 alkyl group that forms a spiro group when both R5 and R6 are part of the same cyclic structure, a C5 to C40 aryl group, a C5 to C40 alkaryl group, a C5 to C40 aralkyl group that optionally forms a spiro group when both R5 and R6 are part of the same cyclic structure, an —OH, and together with one another a C=O;

provided that at least one of R1 and R3 on each ring is an —NH$_2$; and

Formula II is:

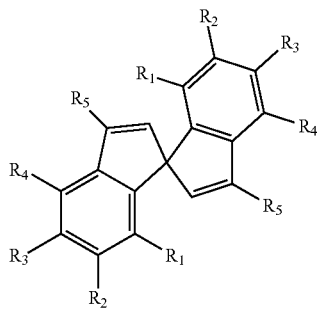

wherein each R1 is independently selected from H, Cl, Br, I, a C1 to C20 linear, cyclic, or branched alkyl group, a C5 to C20 aryl group, a C5 to C20 alkaryl group, a C5 to C20 aralkyl group, and $NH_2$;

each R2 is —OH;

each R3 is independently selected from H, Cl, Br, I, a C1 to C20 linear, cyclic or branched alkyl group, a C5 to C20 aryl group, a C5 to C20 alkaryl group, a C5 to C20 aralkyl group, and $NH_2$;

each R4 is independently selected from H, Cl, Br, I, a C1 to C20 linear, cyclic or branched alkyl group, a C5 to C20 aryl group, a C5 to C20 alkaryl group, and a C5 to C20 aralkyl group;

each R5 is independently selected from an —H, a C1 to C20 linear, cyclic, or branched alkyl group, a C5 to C40 aryl group, a C5 to C40 alkaryl group, and a C5 to C40 aralkyl group;

provided that at least one of R1 and R3 on each ring is an —$NH_2$.

In a further aspect, the present description provides curative compositions for curing fluoroelastomers comprising a curative selected from the group consisting of curatives of Formula I and II, where Formula I is:

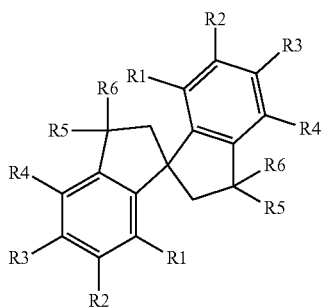

wherein each R1 is independently selected from H, Cl, Br, I, a C1 to C20 linear, cyclic, or branched alkyl group, a C5 to C20 aryl group, a C5 to C20 alkaryl group, a C5 to C20 aralkyl group, and $NH_2$;

each R2 is —OH;

each R3 is independently selected from H, Cl, Br, I, a C1 to C20 linear, cyclic, or branched alkyl group, a C5 to C20 aryl group, a C5 to C20 alkaryl group, a C5 to C20 aralkyl group, and $NH_2$;

each R4 is independently selected from H, Cl, Br, I, a C1 to C20 linear, cyclic, or branched alkyl group, a C5 to C20 aryl group, a C5 to C20 alkaryl group, and a C5 to C20 aralkyl group;

each R5 and R6 is independently selected from an —H, a C1 to C20 linear or branched alkyl group, a C3 to C40 alkyl group that forms a spiro group when both R5 and R6 are part of the same cyclic structure, a C5 to C40 aryl group, a C5 to C40 alkaryl group, a C5 to C40 aralkyl group that optionally forms a spiro group when both R5 and R6 are part of the same cyclic structure, an —OH, and together with one another a C=O;

provided that at least one of R1 and R3 on each ring is an —$NH_2$; and

Formula II is:

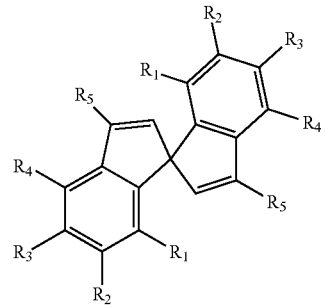

wherein each R1 is independently selected from H, Cl, Br, I, a C1 to C20 linear, cyclic, or branched alkyl group, a C5 to C20 aryl group, a C5 to C20 alkaryl group, a C5 to C20 aralkyl group, and $NH_2$;

each R2 is —OH;

each R3 is independently selected from H, Cl, Br, I, a C1 to C20 linear, cyclic or branched alkyl group, a C5 to C20 aryl group, a C5 to C20 alkaryl group, a C5 to C20 aralkyl group, and $NH_2$;

each R4 is independently selected from H, Cl, Br, I, a C1 to C20 linear, cyclic or branched alkyl group, a C5 to C20 aryl group, a C5 to C20 alkaryl group, and a C5 to C20 aralkyl group;

each R5 is independently selected from an —H, a C1 to C20 linear, cyclic, or branched alkyl group, a C5 to C40 aryl group, a C5 to C40 alkaryl group, and a C5 to C40 aralkyl group;

provided that at least one of R1 and R3 on each ring is an —$NH_2$.

The details of embodiments are set forth in the description below. Other features, objects, and advantages will be apparent from the description and from the claims below.

DETAILED DESCRIPTION

Curative Composition

In some embodiments, curatives described herein may be described as those selected from the group consisting of curatives of Formula I:

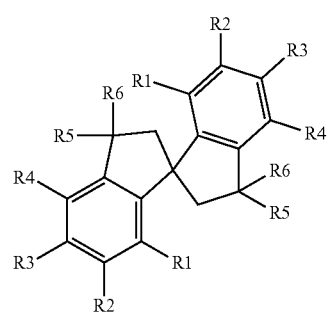

wherein each R1 is independently selected from H, Cl, Br, I, a C1 to C20 linear, cyclic, or branched alkyl group, a C5 to C20 aryl group, a C5 to C20 alkaryl group, a C5 to C20 aralkyl group, and $NH_2$;

each R2 is —OH;

each R3 is independently selected from H, Cl, Br, I, a C1 to C20 linear, cyclic, or branched alkyl group, a C5 to C20 aryl group, a C5 to C20 alkaryl group, a C5 to C20 aralkyl group, and NH$_2$;

each R4 is independently selected from H, Cl, Br, I, a C1 to C20 linear, cyclic, or branched alkyl group, a C5 to C20 aryl group, a C5 to C20 alkaryl group, and a C5 to C20 aralkyl group;

each R5 and R6 is independently selected from an —H, a C1 to C20 linear or branched alkyl group, a C3 to C40 alkyl group that forms a spiro group when both R5 and R6 are part of the same cyclic structure, a C5 to C40 aryl group, a C5 to C40 alkaryl group, a C5 to C40 aralkyl group that optionally forms a spiro group when both R5 and R6 are part of the same cyclic structure, an —OH, and together with one another a C=O;

provided that at least one of R1 and R3 on each ring is an —NH$_2$.

In other embodiments, curatives described herein may be described as those selected from the group consisting of curatives of Formula II:

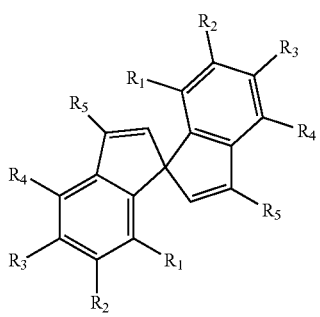

wherein each R1 is independently selected from H, Cl, Br, I, a C1 to C20 linear, cyclic, or branched alkyl group, a C5 to C20 aryl group, a C5 to C20 alkaryl group, a C5 to C20 aralkyl group, and NH$_2$;

each R2 is —OH;

each R3 is independently selected from H, Cl, Br, I, a C1 to C20 linear, cyclic or branched alkyl group, a C5 to C20 aryl group, a C5 to C20 alkaryl group, a C5 to C20 aralkyl group, and NH$_2$;

each R4 is independently selected from H, Cl, Br, I, a C1 to C20 linear, cyclic or branched alkyl group, a C5 to C20 aryl group, a C5 to C20 alkaryl group, and a C5 to C20 aralkyl group;

each R5 is independently selected from an —H, a C1 to C20 linear, cyclic, or branched alkyl group, a C5 to C40 aryl group, a C5 to C40 alkaryl group, and a C5 to C40 aralkyl group;

provided that at least one of R1 and R3 on each ring is an —NH$_2$.

The curatives described herein may be prepared by various synthetic routes, which will, in light of the descriptions provided herein of the preparation of various specific embodiments, be readily ascertained by those of skill in the art.

For instance, the preparation of one particular embodiment of the curatives of Formula I described and claimed herein is provided in the Examples. The preparation of 3,3,3',3'-tetramethyl-1,1'-spirobisindane-6,6'-diol begins with the acid-catalyzed self-condensation of three equivalents of 4,4'-isopropylidene diphenol, commonly referred to as "BPA".

As used herein, the term alkaryl refers to a substituent group that contains an aryl group bonded through a bond to an aromatic atom in an aromatic group, which aromatic group further contains an alkyl substituent. An example of an alkaryl group is a tolyl substituent such as the following:

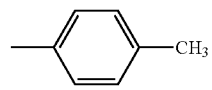

Further, as used herein, the term aralkyl refers to a substituent group that contains an alkyl group bonded through a bond to an alkyl atom in an alkyl group, which alkyl group further contains an aryl substituent. An example of an aralkyl group is a benzyl substituent such as the following:

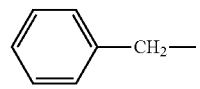

Upon preparation, isolation of the 3,3,3',3'-tetramethyl-1,1'-spirobisindane-6,6'-diol may be carried out by precipitation from common solvents (i.e., methanol, methylene chloride, tetrahydrofuran) using deionized water.

Further derivatization of the aromatic rings in the 3,3,3',3'-tetramethyl-1,1'-spirobisindane-6,6'-diol can be carried out using methods within the skill in the art. For instance, 3,3,3',3'-tetramethyl-5,5'-dinitro-1,1'-spirobisindane-6,6'-diol may be prepared by nitration of 3,3,3',3'-tetramethyl-1,1'-spirobisindane-6,6'-diol by treatment with nitric acid. The nitrated product may then be reduced to the 5,5'-diamino-3,3,3',3'-tetramethyl-1,1'-spirobisindane-6,6'-diol, for instance by treatment with hydrogen gas in the presence of a hydrogenation catalyst.

In some embodiments, 5,5'-diamino-3,3,3',3'-tetramethyl-1,1'-spirobisindane-6,6'-diol may be further reacted under electrophilic aromatic substitution conditions, for instance in the presence of Br$_2$ to replace H with Br in one or more of the R1 or R3 and/or R4 groups.

Further compounds of Formula I include, for instance, those where R5 and R6 together with one another form a C=O, as in the following structure:

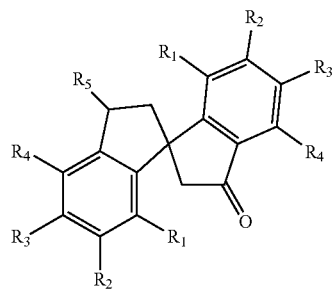

where R1 to R4 are as described above. Such compounds may be prepared, for instance, by an adaptation of the methods described in Organic Letters, 2008, (10), 2641-2643. Compounds of Formula II may similarly be prepared.

Fluoroelastomers

In some embodiments, the fluoroelastomers may include interpolymerized units derived from fluorine-containing monomers, such as tetrafluoroethylene (TFE), chlorotrifluoroethylene (CTFE), vinylidene fluoride, and/or hexafluoropropene. Monomers suitable for preparation of fluoroelastomers include ethylenically-unsaturated monomers represented by the formulas $CF_2=CF-R_f^1$, $CF_2=CF-O-R_f^2$, and $CH_2=CR_2$, wherein $R_f^1$ is a perfluoroalkyl; $R_f^2$ is a perfluoroalkyl, or a perfluoroalkoxy; and each R is independently selected from H, F, Br, I, Cl, or a aliphatic group. In some embodiments, the perfluoroalkyl, perfluoroalkoxy, and aliphatic groups may have F, Br, I, or Cl substituents. In some embodiments, the fluoroelastomers may include interpolymerized units derived from perfluoro alkyl vinyl ether(s), perfluoro alkoxy vinyl ether(s), perfluoro alkene ether(s), and/or perfluoro alkoxy alkene ether(s).

Suitable fluoroelastomers include interpolymerized units derived from a nitrogen-containing cure site monomer. Such fluoroelastomers may further comprise at least two principal monomers in addition to the cure site monomer. Examples of suitable candidates for the principal monomer include perfluoroolefins (e.g., tetrafluoroethylene (TFE) and hexafluoropylene (HFP)), chlorotrifluoroethylene (CTFE), perfluorovinyl ethers (e.g., perfluoroalkyl vinyl ethers and perfluoroalkoxy vinyl ethers), and optionally, hydrogen-containing monomers such as olefins (e.g., ethylene, propylene, and the like), and vinylidene fluoride (VDF). Such fluoroelastomers include, for example, fluoroelastomer gums and perfluoroelastomer gums.

When the fluoroelastomer is halogenated, preferably perfluorinated, it may in some embodiments contain at least 50 mole percent (mol %) of its interpolymerized units derived from TFE and/or CTFE, optionally including HFP. The balance of the interpolymerized units of the fluoroelastomer (10 to 50 mol %) may be made up of one or more perfluoro vinyl ethers and a nitrogen-containing cure site monomer (e.g., a nitrile-containing vinylether or an imidate containing vinylether). The cure site monomer makes up from about 0.1 to about 10 mol % (more preferably from about 0.5 to about 3 mol %) of the elastomer. The compositions of the present description may be, in some embodiments, useful particularly in providing perfluoropolymers such as perfluoroelastomers.

When the fluoroelastomer is not perfluorinated, it may contain from about 5 to about 90 mol % of its interpolymerized units derived from TFE, CTFE, and/or HFP, from about 5 to about 90 mol % of its interpolymerized units derived from VDF, ethylene, and/or propylene, up to about 40 mol % of its interpolymerized units derived from a vinyl ether, and from about 0.1 to about 5 mol % (more preferably from about 1.0 to about 2.5 mol %) of a nitrogen-containing cure site monomer.

In some embodiments, the fluoroelastomer compositions are derived from interpolymerized units of fluorinated monomers such as those having the formula $CF_2=CF-R_f$, wherein $R_f$ is fluorine or a $C_1$-$C_8$ perfluoroalkyl, along with hydrogen-containing $C_2$-$C_9$ olefins, which have less than half of the hydrogen atoms substituted with fluorine, even less than one-fourth of the hydrogen atoms substituted with fluorine, and which are non-fluorinated in other embodiments. In some embodiments, the non-fluorinated olefin is absent.

Hydrogen-containing olefins useful in the compositions described herein include those of the formula $CX_2=CX-R$, wherein each X is, independently, hydrogen or fluorine or chlorine, R is hydrogen, fluorine, or a $C_1$-$C_{12}$, preferably $C_1$-$C_3$, alkyl. Preferred olefins include partially-fluorinated monomers (e.g., vinylidene fluoride) or hydrogen-containing monomers such as olefins including α-olefins (e.g., ethylene, propylene, butene, pentene, hexene, and the like). Combinations of the above-mentioned materials are also useful.

Perfluorinated vinyl ethers also are suitable as comonomers in the present compositions. These include, for example, monomers described in U.S. Pat. Nos. 6,255,536 and 6,294,627 (Worm, et al., herein incorporated by reference) which includes perfluorinated vinyl ethers such as $CF_2=CF(CF_2)_m$-$[O(CF_2)_p]_n$-$OR_f$, including vinyl formals such as $R_fOCF_2OCF=CF_2$, where $R_f$ can contain oxygen, wherein $R_f$ is a linear or branched perfluorinated aliphatic group that may contain oxygen atoms thereby forming additional ether linkages, and wherein m is 0-4, n is 0-6, and p is 1-3, provided that m and n are not both 0.

Such perfluorovinylethers include, for example, $CF_2=CFOCF_3$, $CF_2=CF-O-CF_2-O-CF_3$, $CF_2=CF-O-CF_2-O-CF_2CF_3$, $CF_2=CF-O-CF_2-O-CF_2CF_2CF_3$, $CF_2=CFOCF_2CF_2OCF_3$, $CF_2=CFOCF_2CF_2CF_2OCF_3$, $CF_2=CFOCF_2CF_2CF_3$, $CF_2=CF-O-CF_2CF(CF_3)-O-CF_3$, $CF_2=CFOCF_2CF(CF_3)OCF_2CF_2CF_3$, $CF_2=CF-O-CF_2CF_2-O-CF_2-O-CF_2-O-CF_3$, and $CF_2=CFOCF_2CF(CF_3)OCF_2CF(CF_3)OCF_2CF_2CF_3$.

In addition, the fluoroelastomers described herein may include interpolymerized units of fluoro (alkene ether) monomers, including those described in U.S. Pat. No. 5,891,965 (Worm and Guerra) and U.S. Pat. No. 6,255,535 (Schulz, et al. Such monomers include, for example, $CF_2=CF(CF_2)_m-O-R_f$ wherein m is an integer from 1 to 4, and wherein $R_f$ is a linear or branched perfluoroalkylene group that may include oxygen atoms thereby forming additional ether linkages, and wherein $R_f$ contains from 1-20, more preferably from 1 to 10, carbon atoms in the backbone, and wherein $R_f$ also may contain additional terminal unsaturation sites. $R_f$ groups containing such oxygen atoms are referred to as perfluoroalkyleneoxy groups. Useful monomers include the perfluoroallyl ethers represented by the formula: $CF_2=CF-CF_2-O-R_f$, where $R_f$ is defined above in this paragraph. Exemplary perfluoroalkeneether compounds include those selected from the group consisting of $CF_2=CFCF_2-O-CF_3$, $CF_2=CFCF_2-O-CF_2-O-CF_3$, $CF_2=CFCF_2-O-CF_2CF_2-O-CF_3$, $CF_2=CFCF_2-O-CF_2CF_2-O-CF_2-O-CF_2CF_3$, $CF_2=CFCF_2-O-CF_2CF_2-O-CF_2CF_2CF_2-O-CF_3$, $CF_2=CFCF_2-O-CF_2CF_2-O-CF_2CF_2-O-CF_2-O-CF_3$, $CF_2=CFCF_2CF_2-O-CF_2CF_2CF_3$.

One example of a useful fluoroelastomer is composed of principal monomer units of tetrafluoroethylene and at least one perfluoroalkyl vinyl ether. In such copolymers, the copolymerized perfluorinated ether units constitute from about 1 to about 60 mol % (more preferably 10 to 40 mol %) of total monomer units present in the fluoroelastomer.

One or more other fluoropolymers may be incorporated into the composition in addition to the fluoroelastomers described herein, the fluoroelastomers having interpolymerized units derived from a nitrogen-containing cure site monomer. In addition, one or more other fluoropolymers (which may include one or more copolymers) may be blended with the fluoroelastomer (which may comprise a copolymer) having interpolymerized units derived from a nitrogen-containing cure site monomer. Such other fluoropolymers useful in a blend and/or copolymer include the entire array described above, and including homopolymers and copolymers comprising the interpolymerized units mentioned above. For example, polytetrafluoroethylene (PTFE) and PFA (tetrafluoroethylene-perfluorovinylether) are useful. The other fluoropolymer(s) may lack interpolymerized units derived from a nitrogen-containing cure site monomer and/or may include reactive sites adapted to a selected curative system. For example, two different fluoroelastomers, each having interpolymerized units derived from a nitrogen-containing cure site monomer, such as a monomer comprising a nitrile group, may be blended to provide the fluoroelastomers for the present description.

Another fluoropolymer may be included along with another curative, such as described below, to provide particular properties. For example, a fluoropolymer suitable for peroxide curing and a peroxide curative may be included to improve chemical stability. Such a blend balances the thermal stability and the chemical stability of the resultant blend, and also may provide economic benefits. These other curatives also may be used to cure a blend of fluoroelastomers having nitrogen-containing cure site monomers without the need to include a fluoropolymer lacking a nitrogen-containing cure site monomer.

The fluoroelastomer(s) having nitrogen-containing cure site monomers preferably make up enough of the total fluoropolymer to provide increased thermal stability over a comparative fluoroelastomer that lacks the composition described herein. This amount is generally at least 25 weight percent (wt %), more preferably at least 50 wt %, of the total fluoroelastomer in a composition as described herein. In some embodiments, the fluoroelastomer component is comprised entirely of fluoroelastomer(s) with nitrogen-containing interpolymerized units.

The useful fluoroelastomers may be prepared by known methods. For example, the polymerization process can be carried out by free-radical polymerization of the monomers as an aqueous emulsion polymerization or as a solution polymerization in an organic solvent. When fluoropolymer blends are desired, a preferable route of incorporation is through blending the fluoropolymer latices in the selected ratio, followed by coagulation and drying.

Cure Site Components

Fluoroelastomers described herein include a cure site component, which enables curing the fluoroelastomer. The cure site component can be partially or fully fluorinated. At least one cure site component of at least one fluoroelastomer comprises a nitrogen-containing group. Examples of nitrogen-containing groups useful in the cure site monomers include nitrile, imidate, amidine, amidine salts, amidoxime, amide, imide, and amine-oxide groups.

Useful nitrogen-containing cure site monomers include nitrile-containing fluorinated olefins and nitrile-containing fluorinated vinyl ethers, such as: $CF_2=CFO(CF_2)_L CN$; $CF_2=CFO(CF_2)_u OCF(CF_3)CN$; $CF_2=CF[OCF_2CF(CF_3)]_r O(CF_2)_t CN$; $CF_2=CFO[CF_2CF(CF_3)O]_q (CF_2O)_y CF(CF_3)CN$; and; wherein L=2-12; q=0-4; r=1-2; y=0-6; t=1-4; and u=2-6. Representative examples of such monomers include $CF_2=CFO(CF_2)_3 OCF(CF_3)CN$, perfluoro(8-cyano-5-methyl-3,6-dioxa-1-octene), and $CF_2=CFO(CF_2)_5 CN$ (MV5CN).

Another suitable cure site component may contain a halogen that is capable of participation in a peroxide cure reaction. Such a halogen may be present along a fluoroelastomer chain and/or in a terminal position. Typically the halogen is bromine or iodine, but it may be chlorine. Copolymerization is preferred to introduce the halogen in a position along a fluoroelastomer chain. In this route, a selection of the fluoroelastomer components mentioned above are combined with a suitable fluorinated cure site monomer. Examples of the bromo- or iodo-fluoroolefins include: bromodifluoroethylene, bromotrifluoroethylene, iodotrifluoroethylene, 1-bromo-2,2-difluoroethylene, and 4-bromo-3,3,4,4-tetrafluorobut-1-ene, 4-iodo-3,3,4,4,-tetrafluorobut-1-ene (ITFB), and the like, and examples of the bromo- or iodo-fluorovinyl ethers include: $BrCF_2OCF=CF_2$, $BrCF_2CF_2OCF=CF_2$, $BrCF_2CF_2CF_2OCF=CF_2$, $CF_3CF(Br)CF_2OCF=CF_2$, and the like. In addition, non-fluorinated bromo- or iodo-olefins, e.g., vinyl bromide and 4-bromo-1-butene, can be used. Iodo-fluoroolefins more generally include those of the formula $CH_2=CH(CF_2)_n I$, where n is an integer between 2 and 8.

Yet another useful cure site component includes interpolymerized units having one or more pendant amidoxime structures (i.e., $-C(NR_2)=NOR$ and/or its tautomer $-C(NR-OR)=NR$), and/or pendant amidrazone structures (i.e., $-C(NR_2)=N-NR_2$ and/or its tautomer $-C(NR-NR_2)=NR$), wherein each R is independently selected from the group consisting of hydrogen, and linear or branched, substituted or unsubstituted, perfluorinated, partially-fluorinated, or non-fluorinated, alkyl or aryl groups, optionally containing one or more heteroatoms. In some embodiments, at least one R group is hydrogen. In some embodiments, all of the R groups are hydrogens.

In some embodiments, the amidoxime and/or amidrazone groups can be attached directly to the polymer backbone. In some embodiments, one or more of the amidoxime and/or amidrazone groups may be indirectly attached to the backbone via a substituted or unsubstituted, linear or branched, aliphatic chain interposed between the polymer backbone and the amidoxime and/or amidrazone group. In some embodiments, the amidoxime or amidrazone group is at the terminal position of the aliphatic group; however, the amidoxime or amidrazone group may be present at any position along the aliphatic chain.

In further embodiments, the amidoxime and/or amidrazone groups are attached to the polymer backbone via alkyl groups, e.g., $B-(CZ_2)_n-A$ wherein, A is an amidoxime or amidrazone; B represents the polymer backbone; each Z is independently selected from hydrogen, a halogen (e.g., F or Cl), or an aliphatic group (in some embodiments, an aliphatic group containing 1-8 carbon atoms), which aliphatic group may have halogen substituents; and n=1 to 50, in some embodiments, 1 to 20, or even 1 to 10. In some embodiments, the interposed alkyl chain is perfluorinated, in which case each Z is F.

In some embodiments, the amidoxime and/or amidrazone groups can also be attached by alkoxy side chains, e.g., $B-(CZ_2)_n-(O-R^2)_m-(O-R^3)_p-(CZ_2)_q-CZX-A$, wherein $R^2$ and $R^3$ are independently selected from $C_1$-$C_{10}$ (in some embodiments, $C_1$-$C_5$) alkylenes, which may be linear or branched and which may be hydrogen-containing, partially-halogenated, partially-fluorinated, perhalogenated, or perfluorinated; n and m are each independently 1 to 50, in some embodiments, 1 to 20, or even 1 to 10; p is 0 to 10; q is 0 to 10; each Z is independently a hydrogen, a halogen (e.g., F, Cl, or Br); and X is F or $CF_3$. In some embodiments, the alkoxy side chain is a perfluorinated alkoxy, in which case each Z is F, leading to, e.g., $B-(OCF_2)-(CF_2)_4-A$.

In some embodiments, the amidoxime or amidrazone structure is located at the terminal position of the alkyl or alkoxy side chain. Further, the amidoxime or amidrazone structure may be located at any other position along the side chain. In some embodiments, the amidoxime or amidrazone structure is pendant to a branch on the side chain.

The level of amidoxime and/or amidrazone units in the overall fluoropolymer composition is that amount sufficient to provide the desired physical properties in a selected material after curing. In some embodiments, the level of amidoxime and/or amidrazone units is at least about 0.01 mol %, in some embodiments, at least about 0.1 mol %, in some embodiments, at least about 0.2 mol %, in some embodiments, at least about 0.5 mol %, or even at least about 0.7 mol %. In some embodiments, the level of amidoxime and/or amidrazone units is not greater than about 5 mol %, in some embodiments, not greater than about 3 mol % and, in some embodiments, not greater than about 1 mol %.

The amidoxime and/or amidrazone units may be introduced into the polymer by various means. Such means are described in detail in WO2006/068685 (Grootaert, et al.).

Still further cure site components include interpolymerized units having one or more pendant amidine structures (i.e., $-C(NR_2)=NR$, wherein each R is independently selected from the group consisting of hydrogen, and linear or branched, substituted or unsubstituted, perfluorinated, partially-fluorinated, or non-fluorinated, alkyl or aryl groups, optionally containing one or more heteroatoms. In some embodiments, at least one R group is hydrogen. In some embodiments, all of the R groups are hydrogens.

The amount of cure site component in a side chain position of the fluoroelastomer generally is from about 0.05 to about 5 mol % (more preferably from 1.0 to 2.5 mol %). In fact, as shown in the Examples, surprisingly, when the cure site component is present in an amount of from 1.5 to 2.5 mol %, the compression set value is dramatically lowered when compared to fluoroelastomers containing cure site components at lower levels. In some embodiments, as shown in the Examples, such cure site components are nitrogen-containing cure site components.

The cure site component may also occur in the terminal position of a fluoroelastomer chain. Chain transfer agents or initiators are used to introduce the halogen in a terminal position. Generally, a suitable chain transfer agent is introduced in the reaction medium during polymer preparation, or derived from a suitable initiator.

Examples of useful chain transfer agents include those having the formula $R_fZ_x$ wherein $R_f$ is a substituted or unsubstituted $C_1$-$C_{12}$ fluoroalkyl radical, which may be perfluorinated, Z is Br or I, and x is 1 or 2. Specific examples involving bromine include: $CF_2Br_2$, $Br(CF_2)_2Br$, $Br(CF_2)_4Br$, $CF_2(Cl)Br$, $CF_3CF(Br)CF_2Br$, and the like. Specific examples involving iodine include: $CF_2I_2$, $I(CF_2)_2I$, $I(CF_2)_4I$, $CF_2(Cl)I$, $CF_3CF(I)CF_2I$, and the like. Useful initiators include, e.g., $NaO_2S(CF_2)_xX$, wherein X is Br or I, and n is 1-10.

The amount of cure site component in a terminal position in the fluoroelastomer is generally from about 0.05 to about 5 mol % (more preferably from 0.1 to 2 mol %).

Combinations of cure site components also are useful in the present compositions. For example, a fluoroelastomer containing a halogen that is capable of participation in a peroxide cure reaction may also contain a nitrogen-containing cure site component such as a nitrile group-containing cure site component. Generally, from about 0.1 to about 5 mol % (more preferably from about 0.3 to about 2 mol %) of the total cure site component is incorporated into the fluoropolymer.

Curable Compositions

An effective amount of the curative is used to crosslink the fluoroelastomer. When the amount of curative is too low, the fluoroelastomer may not crosslink sufficiently to develop the desired physical properties and/or may crosslink more slowly than desired. When the amount of curative is too high, the fluoroelastomer may crosslink into a material that is less compliant than desired and/or may crosslink too rapidly for the desired process conditions. The selection of the particular parts of a composition can affect the amount of curative desired. For example, the type and/or amount of filler selected may retard or accelerate curing relative to a similar, but unfilled, composition, requiring an appropriate adjustment in the amount of curative that is known to those skilled in the field. In another example, when the curative is hygroscopic, the type and/or amount of filler in the composition may alter the hygroscopic nature of the curative composition.

The composition of the fluoroelastomer also affects the desired amount of one or more curatives. For example, when a blend of a fluoroelastomer with interpolymerized units of a nitrogen-containing cure site monomer and another fluoropolymer lacking nitrogen-containing cure sites is used, an effective amount of a first selected curative can be used to crosslink the fluoroelastomer having interpolymerized units derived from a nitrogen-containing cure site monomer together with an effective amount of a second selected curative used to crosslink the other fluoropolymer. The first and second selected curatives may have the same or different composition. That is, either one or both selected curatives may function to crosslink either one or both fluoropolymers, Generally, the effective amount of curative, which may include more than one composition, is at least about 0.1 parts curative per hundred parts of gum on a weight basis (phr), preferably at least about 0.5 phr. The effective amount of curative generally is below about 10 phr, preferably below about 5 phr.

The fluoroelastomer composition curing can also be modified by using other types of curatives along with the curatives described herein. Examples of such curatives are known and include bis-aminophenols (e.g., U.S. Pat. Nos. 5,767,204 and 5,700,879), bis-amidooximes (e.g., U.S. Pat. No. 5,621,145), and ammonium salts (e.g., U.S. Pat. No. 5,565,512). In addition, organometallic compounds of arsenic, antimony, and tin can be used (e.g., U.S. Pat. Nos. 4,281,092, and 5,554,680). Particular examples include allyl-, propargyl-, triphenyl-allenyl-, and tetraphenyltin and triphenyltin hydroxide.

Further, other types of curatives may include those having the following general formula:

wherein m, n, p, and q are positive integers, wherein m*p=n*q, wherein $Q^{m+}$ is an organo onium, and $A^{q-}$ is an anion, provided that at least one $A^{q-}$ is selected from Formula II:

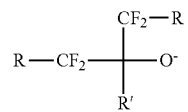

wherein each R independently is H, halo, alkyl, aryl, aralkyl, alkaryl, or cycloalkyl, and which also may be halogenated, fluorinated, or perfluorinated, wherein two or more of R and R' groups may together form a ring, wherein each R group independently may contain one or more heteroatom(s), wherein R' can be the same as R, with the proviso that R' cannot be halo.

Other useful other types of curatives include those having the formula:

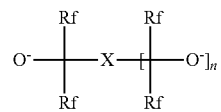

wherein each $R_f$ independently is $R-CF_2$ or a perfluoroalkyl group having from 1 to 8 carbon atoms, wherein R is H, halo, alkyl, aryl, alkaryl, aralkyl, or cycloalkyl, having up to 8 carbon atoms and which also may be halogenated, fluorinated, or perfluorinated, and which may contain a heteroatom, wherein X is a linking group, and wherein n is a positive integer.

In yet further embodiments, other types of curatives may include those of the formula:

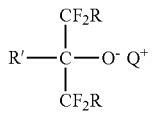

wherein Q+ is a non-interfering organophosphonium, organosulfonium, or organoammonium cation; each R independently represents H, halogen, a hydrocarbyl group or a halogenated hydrocarbyl group, wherein at least one carbon atom of the hydrocarbyl group may be further substituted with one or more heteroatoms selected from N, O and S; R' represents H, a hydrocarbyl group, or a halogenated hydrocarbyl group, wherein at least one carbon atom of the hydrocarbyl group may be further substituted with one or more heteroatoms selected from N, O and S; or any two of R and R' may together form a divalent hydrocarbylene group, wherein at least one carbon atom of the hydrocarbylene group may be further substituted by one or more heteroatoms selected from N, O and S.

In still further embodiments, other curatives may include those of the general formula:

$\{RA\}^{(-)}\{QR'_k\}^{(+)}$ or the precursors thereof added separately or as a mixture; and optionally an alcohol of the general formula $R^2$—OH, wherein $R^2$ is an alkyl group having from 1 to 20 carbon atoms, and wherein $R^2$ can be fluorinated. In this embodiment, R is a $C_1$-$C_{20}$ alkyl or alkenyl, $C_3$-$C_{20}$ cycloalkyl or cycloalkenyl, or $C_6$-$C_{20}$ aryl, aralkyl, or alkaryl. R can contain at least one heteroatom, i.e., a non-carbon atom such as O, P, S, and N, such as an ether linkage. R can also be substituted, such as where one or more hydrogen atoms in the group is replaced with F, Cl, Br, or I. Each R can be perfluorinated, partially fluorinated, or non-fluorinated. A is an acid anion or an acid derivative anion, e.g., A can be COO, $SO_3$, $SO_2$, $SO_2NH$, $PO_3$, $CH_2OPO_3$, $(CH_2O)_2PO_2$, $C_6H_4O$, $OSO_3$, O (in the cases where R is aryl or alkylaryl),

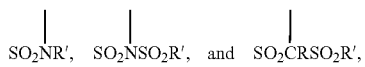

preferably COO, O, $C_6H_4O$, $SO_3$, $OSO_3$, or

most preferably COO, O, $SO_3$, and $OSO_3$; R' is defined as R (above), and a particular selection for R' may be the same or different from the R attached to A, and one or more A groups may be attached to R. Q is phosphorous (P), sulfur (S), nitrogen (N), arsenic (As), or antimony (Sb), and k is the valence of Q. Each R' is, independently, hydrogen or a substituted or unsubstituted alkyl, aryl, aralkyl, alkaryl, or alkenyl group having from 1 to 20 carbon atoms, provided that when Q is nitrogen and the fluoropolymer in the composition consists essentially of a terpolymer of TFE, a perfluorovinylether, and a perfluorovinylether cure site monomer comprising a nitrile group not every R' is H. That is, when the specified terpolymer is the only fluoropolymer in a composition, the group $QR'_k$ is not $NH_4$, however, $NR'_4$, $NHR'_3$, $NH_2R'_2$, and $NH_3R'$ all fall within the scope of certain embodiments of the present invention. For example, when the cure site monomer is a nitrile-containing partially-fluorinated vinyl ether, the group $QR'_k$ can be $NH_4$.

Examples of suitable substituents include halogen (e.g., chlorine, fluorine, bromine, iodine), cyano, $OR^3$, and $COOR^3$ groups wherein $R^3$ is selected from hydrogen or the alkali or alkaline earth metals, of which H, K, Na, and $NH_4$, are preferred, $C_1$ to $C_{20}$ alkyl, aryl, aralkyl, alkaryl, alkenyl, and R (as described above) groups. In addition, any pair of said R' groups may be connected to each other and the Q atom to form a heterocyclic ring.

Further discussion of other curatives suitable for the compositions, methods, and articles described herein may be found in U.S. Pat. No. 7,402,630 (Grootaert, et al.); U.S. Pat. No. 7,294,677 (Grootaert, et al.); and U.S. Pat. No. 6,890,995 (Kolb, et al.).

Adjuvants and Additives

Additives such as carbon black, stabilizers, plasticizers, lubricants, fillers including silica and fluoropolymer fillers (e.g., PTFE and/or PFA (perfluoroalkoxy) fillers), and processing aids typically utilized in fluoropolymer compounding can be incorporated into the compositions described herein, provided that they have adequate stability for the intended service conditions. In some embodiments, additives that detrimentally affect the clarity of the composition are avoided. In particular, low temperature performance can be enhanced by incorporation of perfluoropolyethers, as described above.

Fillers such as silica and/or carbon black fillers can be used to balance properties such as modulus, tensile strength, elongation, hardness, abrasion resistance, conductivity, and processability of the compositions. Suitable examples include fumed silica, such as, for example fumed silica commercially available under the trade designation "Aerosil" from Degussa AG, and carbon blacks such as MT blacks (medium thermal black) designated N-991, N-990, N-908, and N-907; FEF N-550; and large particle size furnace blacks. When carbon black is used, 1 to 70 parts filler per hundred parts fluoropolymer (phr) generally is sufficient.

One or more acid acceptors can also be added to the compositions. However, where the presence of extractable metallic compounds is undesirable (such as for semiconductor applications) the use of inorganic acid acceptors can be minimized, and or avoided altogether. Commonly used acid acceptors include, for example, zinc oxide, calcium hydroxide, calcium carbonate, magnesium oxide, silicon dioxide (silica), etc. These compounds generally are used to bind any HF or other acids that might be generated at the high temperatures such as may be encountered during curing steps or at the temperatures of end use.

Preparation of Curable Compositions

The curable compositions described herein may also be combined with other curable compositions such as peroxide-curable fluoropolymer compositions. These additional curable fluoropolymer compositions may also employ small amounts of cure site monomers as a comonomer. Suitable cure site monomers are those which, when combined with a curative (e.g., a peroxide) and, preferably a coagent, will provide a cured composition. Preferably these cure site monomers include at least one halo group (e.g., a bromo or an iodo group).

The curable compositions described herein can be prepared by mixing one or more fluoropolymer(s), the curative, any selected additive or additives, any additional curatives (if desired), and any other adjuvants (if desired) in conventional rubber processing equipment. The desired amounts of compounding ingredients and other conventional adjuvants or ingredients can be added to the unvulcanized fluorocarbon gum stock and intimately admixed or compounded therewith by employing any of the usual rubber mixing devices such as internal mixers, (e.g., Banbury mixers), roll mills, or any other convenient mixing device. The temperature of the mixture during the mixing process typically is kept safely below the curing temperature of the composition. Thus, the temperature typically should not rise above about 120° C. During mixing, it generally is preferable to distribute the components and adjuvants uniformly throughout the gum.

Articles Prepared from Curable Compositions

The mixture is then processed and shaped, such as by extrusion (e.g., into the shape of a film, tube, or hose) or by molding (e.g., in the form of sheet or an O-ring). The shaped article can then be heated to cure the fluoropolymer composition and form a cured article.

Molding or press curing of the compounded mixture usually is conducted at a temperature sufficient to cure the mixture in a desired time duration under a suitable pressure. Generally, this is between about 95° C. and about 230° C., preferably between about 150° C. and about 205° C., for a period of from about 1 minute to 15 hours, typically from 5 minutes to 30 minutes. A pressure of between about 700 kPa and about 21,000 kPa is usually imposed on the compounded mixture in a mold. The molds may be first coated with a release agent and baked.

The molded mixture or press-cured article is then usually post-cured (e.g., in an oven) at a temperature and for a time sufficient to complete the curing, usually between about 150° C. and about 300° C., typically at about 230° C., for a period of from about 2 hours to 50 hours or more, generally increasing with the cross-sectional thickness of the article. For thick sections, the temperature during the post cure is usually raised gradually from the lower limit of the range to the desired maximum temperature. The maximum temperature used is preferably about 300° C., and this value is held for about 4 hours or more. This post-cure step generally completes the cross-linking and may also release residual volatiles from the cured compositions. One example of a suitable post-cure cycle involves exposing molded parts to heat under nitrogen or air using several stages of conditions They can also be post-cured in nitrogen or air using no such staged conditions, at several temperatures, typically between 230 and 300° C.

The fluoropolymer compositions are useful in production of articles such as O-rings, gaskets, tubing, and seals, especially when a clear perfluoroelastomer article is desired. Such articles are produced by molding a compounded formulation of the fluoropolymer composition with various additives under pressure, curing the article, and then subjecting it to a post-cure cycle. The curable compositions formulated without inorganic acid acceptors are particularly well suited for applications such as seals and gaskets for manufacturing semiconductor devices, and in seals for high temperature automotive uses.

Exemplary Embodiments Include The Following:

Embodiment 1. A curable composition comprising a fluoroelastomer comprising a nitrogen-containing cure site monomer and a curative selected from the group consisting of curatives of Formula I and II, where Formula I is:

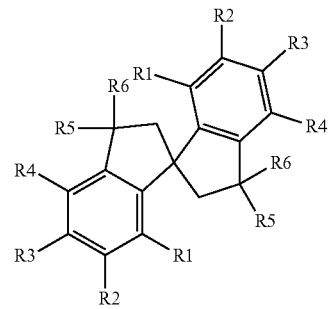

wherein each R1 is independently selected from H, Cl, Br, I, a C1 to C20 linear, cyclic, or branched alkyl group, a C5 to C20 aryl group, a C5 to C20 alkaryl group, a C5 to C20 aralkyl group, and NH$_2$;

each R2 is —OH;

each R3 is independently selected from H, Cl, Br, I, a C1 to C20 linear, cyclic, or branched alkyl group, a C5 to C20 aryl group, a C5 to C20 alkaryl group, a C5 to C20 aralkyl group, and NH$_2$;

each R4 is independently selected from H, Cl, Br, I, a C1 to C20 linear, cyclic, or branched alkyl group, and a C5 to C20 aryl group, a C5 to C20 alkaryl group, a C5 to C20 aralkyl group;

each R5 and R6 is independently selected from an —H, a C1 to C20 linear or branched alkyl group, a C3 to C40 alkyl group that forms a spiro group when both R5 and R6 are part of the same cyclic structure, a C5 to C40 aryl group, a C5 to C40 alkaryl group, a C5 to C40 aralkyl group that optionally forms a spiro group when both R5 and R6 are part of the same cyclic structure, an —OH, and together with one another a C=O;

provided that at least one of R1 and R3 on each ring is an —NH$_2$; and

Formula II is:

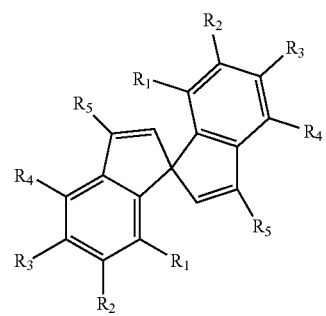

wherein each R1 is independently selected from H, Cl, Br, I, a C1 to C20 linear, cyclic, or branched alkyl group, a C5 to C20 aryl group, a C5 to C20 alkaryl group, a C5 to C20 aralkyl group, and NH$_2$;

each R2 is —OH;

each R3 is independently selected from H, Cl, Br, I, a C1 to C20 linear, cyclic or branched alkyl group, a C5 to C20 aryl group, a C5 to C20 alkaryl group, a C5 to C20 aralkyl group, and NH$_2$;

each R4 is independently selected from H, Cl, Br, I, a C1 to C20 linear, cyclic or branched alkyl group, a C5 to C20 aryl group, a C5 to C20 alkaryl group, and a C5 to C20 aralkyl group;

each R5 is independently selected from an —H, a C1 to C20 linear, cyclic, or branched alkyl group, a C5 to C40 aryl group, a C5 to C40 alkaryl group, and a C5 to C40 aralkyl group;

provided that at least one of R1 and R3 on each ring is an —NH$_2$.

Embodiment 2. A curable composition according to embodiment 1 wherein each R1 and R4 is hydrogen.

Embodiment 3. A curable composition according to either of embodiment 1 or 2, wherein each R5 and R6 of formula I is selected from a —H and a —CH$_3$.

Embodiment 4. A curable composition according to any of embodiments 1 to 3, wherein each R5 and R6 of formula I is —CH$_3$.

Embodiment 5. A curable composition according to any of embodiments 1 to 4 wherein R5 of formula II is a phenyl group.

Embodiment 6. A curable composition according to any of embodiments 1 to 5, wherein the fluoroelastomer is perfluorinated.

Embodiment 7. A curable composition according to any of embodiments 1 to 6, wherein the fluoroelastomer is a copolymer comprising tetrafluoroethylene, perfluoromethylvinylether, and a cyano-containing cure site monomer.

Embodiment 8. A curable composition according to embodiment 7 wherein the cyano-containing cure site monomer is 8-cyano-2-oxaperfluoro-1-oxtene.

Embodiment 9. A curable composition according to any of embodiments 1 to 8, wherein the fluoroelastomer comprises interpolymerized units of from 50 to 75 mole percent of tetrafluoroethylene; from 25 to 45 mole percent of perfluoromethylvinylether; and from 0.5 to 5 mole percent of a cure site monomer.

Embodiment 10. A curable composition according to any of embodiments 1 to 5, wherein the fluoroelastomer is partially fluorinated.

Embodiment 11. A curable composition according to embodiment 10, wherein the fluoroelastomer comprises interpolymerized units of from 20 to 80 mole percent vinylidene fluoride.

Embodiment 12. A curable composition according to any of embodiments 1 to 11, further comprising carbon black.

Embodiment 13. A method comprising curing a curable composition according to any of embodiments 1 to 12.

Embodiment 14. A cured article prepared by the method of embodiment 13.

Embodiment 15. A curative composition for curing fluoroelastomers comprising a curative selected from the group consisting of curatives of Formula I and II, where Formula I is:

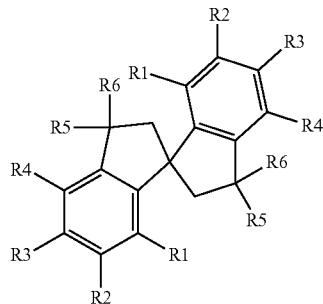

wherein each R1 is independently selected from H, Cl, Br, I, a C1 to C20 linear, cyclic, or branched alkyl group, a C5 to C20 aryl group, a C5 to C20 alkaryl group, a C5 to C20 aralkyl group, and NH$_2$;

each R2 is —OH;

each R3 is independently selected from H, Cl, Br, I, a C1 to C20 linear, cyclic, or branched alkyl group, a C5 to C20 aryl group, a C5 to C20 alkaryl group, a C5 to C20 aralkyl group, and NH$_2$;

each R4 is independently selected from H, Cl, Br, I, a C1 to C20 linear, cyclic, or branched alkyl group, and a C5 to C20 aryl group, a C5 to C20 alkaryl group, a C5 to C20 aralkyl group;

each R5 and R6 is independently selected from an —H, a C1 to C20 linear or branched alkyl group, a C3 to C40 alkyl group that forms a spiro group when both R5 and R6 are part of the same cyclic structure, a C5 to C40 aryl group, a C5 to C40 alkaryl group, a C5 to C40 aralkyl group that optionally forms a spiro group when both R5 and R6 are part of the same cyclic structure, an —OH, and together with one another a C═O;

provided that at least one of R1 and R3 on each ring is an —NH$_2$; and

Formula II is:

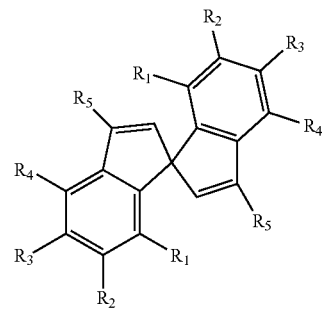

wherein each R1 is independently selected from H, Cl, Br, I, a C1 to C20 linear, cyclic, or branched alkyl group, a C5 to C20 aryl group, a C5 to C20 alkaryl group, a C5 to C20 aralkyl group, and NH$_2$;

each R2 is —OH;

each R3 is independently selected from H, Cl, Br, I, a C1 to C20 linear, cyclic or branched alkyl group, a C5 to C20 aryl group, a C5 to C20 alkaryl group, a C5 to C20 aralkyl group, and NH$_2$;

each R4 is independently selected from H, Cl, Br, I, a C1 to C20 linear, cyclic or branched alkyl group, a C5 to C20 aryl group, a C5 to C20 alkaryl group, and a C5 to C20 aralkyl group;

each R5 is independently selected from an —H, a C1 to C20 linear, cyclic, or branched alkyl group, a C5 to C40 aryl group, a C5 to C40 alkaryl group, and a C5 to C40 aralkyl group;

provided that at least one of R1 and R3 on each ring is an —NH$_2$.

EXAMPLES

Unless otherwise noted, all parts, percentages, ratios, etc. in the examples and the rest of the specification are by weight, and all reagents used in the examples were obtained, or are available, from general chemical suppliers such as, for example, Sigma-Aldrich Company, Saint Louis, Mo., or may be synthesized by conventional methods.

These abbreviations are used in the following examples: phr=parts per hundred rubber; g=grams, min=minutes, mol=mole; mmol=millimole, hr=hour, °C.=degrees Celsius, mL=milliliter, L =liter, psi=pounds per square inch, MPa=megapascals, FTNMR=Fourier transform nuclear magnetic resonance, and N-m=Newton-meter.

| MATERIALS TABLE | |
|---|---|
| TFE | Tetrafluoroethylene |
| PMVE | Perfluoro(methyl vinyl ether) |
| MV5CN | $CF_2=CFO(CF_2)_5CN$ |
| PFE 131 TZ | Perfluoroelastomer, 52.5% TFE, 43.8% PMVE and 3.7% MV5CN (wt %), commercially available from 3M Company, St.Paul, MN |
| PFE 191 TZ | Perfluoroelastomer, 47.8% TFE, 43.8% PMVE and 5.2% MV5CN (wt %), commercially available from 3M Company, St.Paul, MN |
| N990 | Carbon black commercially available from Cabot, Boston, MA |
| Spirobisindane Curative | 5,5'-diamino-3,3,3',3'-tetramethyl-1,1'-spirobisindane-6,6'-diol |
| BPA | 4,4'-isopropylidene diphenol (bisphenol A) commercially available from Sigma Aldrich |

Cure Rheology

Cure rheology tests were carried out using uncured, compounded samples using a rheometer marketed under the trade designation Monsanto Moving Die Rheometer (MDR) Model 2000 by Monsanto Company, Saint Louis, Mo., in accordance with ASTM D 5289-93a at 177° C., no pre-heat, 30 minute elapsed time, and a 0.5 degree arc. Both the minimum torque ($M_L$) and highest torque attained during a specified period of time when no plateau or maximum torque ($M_H$) was obtained were measured. Also measured were the time for the torque to increase 2 units above $M_L$ ($t_s2$), the time for the torque to reach a value equal to $M_L+0.5(M_H-M_L)$, (t'50), and the time for the torque to reach $M_L+0.9(M_H-M_L)$, (t'90) as well as the tandelta at $M_H$. Results are reported in Table 1.

O-Ring Molding and Compression Set

O-rings having a cross-section thickness of 0.139 inch (3.5 mm) were molded (12 min cure at 177° C.) followed by a postcure in nitrogen according to the following ramp-up procedure: Room temperature to 150° C. over 1 hr, hold at 150° C. for 3 hrs, 150° C. to 300° C. over 2 hrs, hold at 300° C. for 8 hrs, 300° C. to room temperature over 2 hrs.

The O-rings were subjected to compression set testing according to ASTM 395-89 method B, with 25% initial deflection.

Preparation of 3,3,3',3'-Tetramethyl-1,1'-spirobisindane-6,6'-diol

In a 5.0 L round bottomed flask, 1000.69 g (4.38 moles) of 4,4'-isopropylidene diphenol (BPA) was melted. Once all of the BPA was melted, 50.51 g (0.526 moles) of methane sulfonic acid was slowly added. The reaction mixture was stirred for 3 hours under a nitrogen atmosphere maintaining the temperature of the reaction mixture between 135-150° C. After 3 hrs, while still hot, the molten reaction mixture was poured into 2.0 L of deionized water. A brown precipitate formed. The resulting precipitate was isolated by vacuum filtration and washed with 1.5 L of deionized water. The isolated solid was then put back in the 5.0 L round bottomed flask and 1.5 L of methylene chloride ($CH_2Cl_2$) was added. The solid was stirred in the $CH_2Cl_2$ at reflux for one hr. The flask was allowed to cool to room temperature and then was placed in a refrigerator (0° C.) overnight. The solid was isolated by vacuum filtration and washed with a minimal amount (500 mL) of chilled $CH_2Cl_2$. The solid was placed in a 4.0 L Erlenmeyer flask and dissolved in 900 mL of methanol. To this solution was added 190 mL of $CH_2Cl_2$. The solution remained clear. The solution was stirred and 1.1 L of deionized water was added in portions. A white precipitate formed. The mixture was placed in a refrigerator (0° C.) overnight. The solid was isolated by vacuum filtration and washed with a minimal amount (300 mL) of chilled $CH_2Cl_2$. The methanol/$CH_2Cl_2$/$H_2O$ precipitation was repeated once more. The solid from the second precipitation was dried in a vacuum oven at 85° C. overnight to yield 214.77 g (48%) of 3,3,3',3'-tetramethyl-1,1'-spirobisindane-6,6'-diol. $^1$H NMR (500 MHz, acetone-$d_6$) δ 7.85 (s, 2H), 7.02 (d, J=8.1 Hz, 2H), 6.68 (dd, J=8.1, 2.4 Hz, 2H), 6.19 (d, J=2.4 Hz, 2H), 2.32 (d, J=13.0 Hz, 2H), 2.19 (d, J=13.0 Hz, 2H), 1.35 (s, 6H), 1.29 (s, 6H).

Preparation of 3,3,3',3'-Tetramethyl-5,5'-dinitro-1,1'-spirobisindane-6,6'-diol and 3,3,3',3'-Tetramethyl-5,7'-dinitro-1,1'-spirobisindane-6,6'-diol A suspension of 3,3,3',3'-tetramethyl-1,1'-spirobisindane-6,6'-diol (30.0 g, 97.4 mmol) in 800 mL of $CH_2Cl_2$ was cooled in an ice bath. Nitric acid (70%, 12.4 mL, 196 mmol) was then added dropwise while maintaining the temperature of the reaction mixture under 10° C. The reaction mixture was stirred overnight and allowed to warm to ambient temperature. The reaction mixture was then passed through a column of $SiO_2$ (7×10 cm) eluting with additional $CH_2Cl_2$. The filtrate was then concentrated to about 200 mL, treated with 80 g of $SiO_2$, and concentrated to dryness. This adsorbed material on $SiO_2$ was applied to a column of $SiO_2$ (500 g) and eluted with a 1:1 mixture of toluene/hexanes. Pure fractions 3,3,3',3'-tetramethyl-5,5'-dinitro-1,1'-spirobisindane-6,6'-diol containing were concentrated to give 13.6 g of yellow solid. $^1$H NMR (500 MHz, CDCl$_3$) δ 10.60 (s, 2H), 7.91 (s, 2H), 6.53 (s, 2H), 2.42 (d, J=13.3 Hz, 2H), 2.29 (d, J=13.3 Hz, 2H), 1.44 (s, 6H), 1.37 (s, 6H). Further elution with toluene followed by $CH_2Cl_2$ gave another 7.3 g of a mixture of 3,3,3',3'-tetramethyl-5,5'-dinitro-1,1'-spirobisindane-6,6'-diol and 3,3,3',3'-tetramethyl-5,7'-dinitro-1,1'-spirobisindane-6,6'-diol. $^1$H NMR (500 MHz, CDCl$_3$) δ 10.65 (s, 1H), 10.55 (s, 1H), 7.88 (s, 1H), 7.42 (d, J=8.6 Hz, 1H), 7.22 (d, J=8.6 Hz, 1H), 6.39 (s, 1H), 2.66 (d, J=13.0 Hz, 1H), 2.46 (d, J=13.0 Hz, 1H), 2.32 (d, J=12.9 Hz, 1H), 2.18 (d, J=13.0 Hz, 1H), 1.52 (s, 3H), 1.41 (s, 3H), 1.37 (s, 3H), 1.36 (s, 3H).

Preparation of 5,5'-Diamino-3,3,3',3'-tetramethyl-1,1'-spirobisindane-6,6'-diol 3,3,3',3'-Tetramethyl-5,5'-dinitro-1,1'-spirobisindane-6,6'-diol (9.5 g) was suspended in 150 mL of ethyl acetate and the mixture was placed in a pressure bottle. Catalyst (5%

Pt/C, 200 mg) was added and the mixture was shaken under 0.28 MPa (40 PSI) of $H_2$ overnight. The reaction mixture was purged with nitrogen and filtered through a Celite pad eluting with a mixture of methanol/$CH_2Cl_2$. The filtrate was concentrated to give 7.5 g of 3,3,3',3'-tetramethyl-5,5'-diamino-1,1'-spirobisindane-6,6'-diol (Spirobisindane) as a gray powder. $^1$H NMR (500 MHz, $CDCl_3$) δ 6.55 (s, 2H), 6.13 (s, 2H), 2.21 (d, J=12.8 Hz, 2H), 2.07 (d, J=12.8 Hz, 2H), 1.30 (s, 6H), 1.24 (s, 6H).

Example 1

100 phr PFE 131 TZ, 30 phr N990 and 2 phr spirobisindane curative made as above was compounded on a two-roll mill. O-rings were molded, cured and tested as per "O-RING MOLDING AND COMPRESSION SET" and compressions set is reported in Table 1.

Example 2

100 phr PFE 191 TZ, 30 phr N990 and 2 phr spirobisindane curative was compounded on a two-roll mill. O-rings were molded, cured and tested as per "O-RING MOLDING AND COMPRESSION SET" and compressions set is reported in Table 1.

Example 3

Identical to Example 1 except that the spiroindane used had a mixture of isomers. The mixture of dintro derivatives 3,3,3',3'-Tetramethyl-5,5'-dinitro-1,1'-spirobisindane-6,6'-diol and 3,3',3'-Tetramethyl-5,7'-dinitro-1,1'-spirobisindane-6,6'-diol were suspended in 150 mL of ethyl acetate and reduced as per "Preparation of 5,5'-Diamino-3,3,3',3'-tetramethyl-1,1'-spirobisindane-6,6'-diol" but the resultant product was a mixture of the 5, 5' and 5, 7' diamino compounds.

TABLE 1

| Material | EX1 | EX2 | EX3 |
| --- | --- | --- | --- |
| PFE 131 TZ | 100 | 0 | 100 |
| PFE 191 TZ | 0 | 100 | 0 |
| N990 | 20 | 20 | 20 |
| spirobisindane | 2 | 2 | 2 |
| MDR (12 min @ 177° C.) | | | |
| $M_L$, in-lb (N-m) | 0.85 | 1.82 | 0.71 |
| $M_H$, in-lb (N-m) | 15.18 | 22.29 | 13.33 |
| $t_s2$, min | 2.96 | 1.51 | 3.75 |
| t'50, min | 5.88 | 5.19 | 6.60 |
| t'90, min | 8.69 | 9.93 | 9.11 |
| Tandelta @ $M_H$ | 0.06 | 0.02 | 0.08 |
| Compression set % (72 hrs @ 270° C.) | 32.3 | 6.9 | 33.1 |
| Compression set % (72 hrs @ 300° C.) | 57.6 | NT | 61.6 |

NT = not tested

We claim:

1. A curable composition comprising a fluoroelastomer, the fluoroelastomer comprising a nitrogen-containing cure site monomer, wherein the composition further comprises a curative selected from the group consisting of curatives of Formula I and curatives of Formula II, where Formula I is:

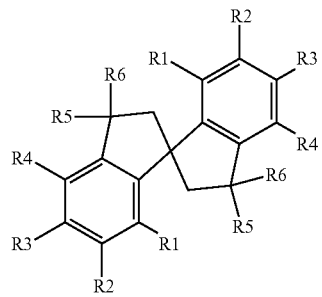

wherein each R1 is independently selected from H, Cl, Br, I, a C1 to C20 linear, cyclic, or branched alkyl group, a C5 to C20 aryl group, a C5 to C20 alkaryl group, a C5 to C20 aralkyl group, and $NH_2$;

each R2 is —OH;

each R3 is independently selected from H, Cl, Br, I, a C1 to C20 linear, cyclic, or branched alkyl group, a C5 to C20 aryl group, a C5 to C20 alkaryl group, a C5 to C20 aralkyl group, and $NH_2$;

each R4 is independently selected from H, Cl, Br, I, a C1 to C20 linear, cyclic, or branched alkyl group, and a C5 to C20 aryl group, a C5 to C20 alkaryl group, a C5 to C20 aralkyl group;

each R5 and R6 is independently selected from an —H, a C1 to C20 linear or branched alkyl group, a C3 to C40 alkyl group that forms a spiro group when both R5 and R6 are part of the same cyclic structure, a C5 to C40 aryl group, a C5 to C40 alkaryl group, a C5 to C40 aralkyl group that optionally forms a spiro group when both R5 and R6 are part of the same cyclic structure, an —OH, and together with one another a C=O;

provided that at least one of R1 and R3 on each ring is an —$NH_2$; and

Formula II is:

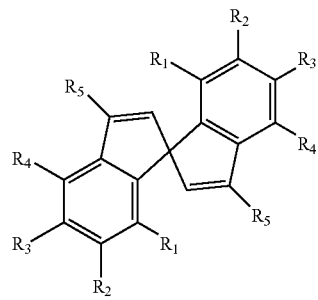

wherein each R1 is independently selected from H, Cl, Br, I, a C1 to C20 linear, cyclic, or branched alkyl group, a C5 to C20 aryl group, a C5 to C20 alkaryl group, a C5 to C20 aralkyl group, and $NH_2$;

each R2 is —OH;

each R3 is independently selected from H, Cl, Br, I, a C1 to C20 linear, cyclic or branched alkyl group, a C5 to C20 aryl group, a C5 to C20 alkaryl group, a C5 to C20 aralkyl group, and $NH_2$;

each R4 is independently selected from H, Cl, Br, I, a C1 to C20 linear, cyclic or branched alkyl group, a C5 to C20 aryl group, a C5 to C20 alkaryl group, and a C5 to C20 aralkyl group;

each R5 is independently selected from an —H, a C1 to C20 linear, cyclic or branched alkyl group, a C5 to C40 aryl group, a C5 to C40 alkaryl group, and a C5 to C40 aralkyl group;

provided that at least one of R1 and R3 on each ring is an —NH$_2$.

2. A curable composition according to claim 1 wherein each R1 and R4 is hydrogen.

3. A curable composition according to claim 1, wherein each R5 and R6 of formula I is selected from a —H and a —CH$_3$.

4. A curable composition according to claim 1, wherein each R5 and R6 of formula I is —CH$_3$.

5. A curable composition according to claim 1, wherein R5 of formula II is a phenyl group.

6. A curable composition according to claim 1, wherein the fluoroelastomer is perfluorinated.

7. A curable composition according to claim 1, wherein the fluoroelastomer is a copolymer comprising tetrafluoroethylene, perfluoromethylvinylether, and a cyano-containing cure site monomer.

8. A curable composition according to claim 7 wherein the cyano-containing cure site monomer is 8-cyano-2-oxaperfluoro-1-oxtene.

9. A curable composition according to claim 1, wherein the fluoroelastomer comprises interpolymerized units of from 50 to 75 mole percent of tetrafluoroethylene; from 25 to 45 mole percent of perfluoromethylvinylether; and from 0.5 to 5 mole percent of a cure site monomer.

10. A curable composition according to claim 1, wherein the fluoroelastomer is partially fluorinated.

11. A curable composition according to claim 10, wherein the fluoroelastomer comprises interpolymerized units of from 20 to 80 mole percent vinylidene fluoride.

12. A curable composition according to claim 1, further comprising carbon black.

13. A method comprising curing a curable composition according to claim 1.

14. A cured article prepared by the method of claim 13.

* * * * *